US010772701B2

(12) United States Patent
McDowall et al.

(10) Patent No.: US 10,772,701 B2
(45) Date of Patent: Sep. 15, 2020

(54) METHOD AND APPARATUS TO PROJECT LIGHT PATTERN TO DETERMINE DISTANCE IN A SURGICAL SCENE

(71) Applicant: Intuitive Surgical Operations, Inc., Sunnyvale, CA (US)

(72) Inventors: Ian E. McDowall, Woodside, CA (US); Brian D. Hoffman, Mountain View, CA (US); Theodore W. Rogers, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 31 days.

(21) Appl. No.: 16/116,296

(22) Filed: Aug. 29, 2018

(65) Prior Publication Data

US 2019/0060013 A1 Feb. 28, 2019

Related U.S. Application Data

(60) Provisional application No. 62/551,677, filed on Aug. 29, 2017.

(51) Int. Cl.
*A61B 90/30* (2016.01)
*A61B 34/35* (2016.01)
(Continued)

(52) U.S. Cl.
CPC .............. *A61B 90/30* (2016.02); *A61B 1/06* (2013.01); *A61B 1/0607* (2013.01);
(Continued)

(58) Field of Classification Search
CPC ....... A61B 1/06; A61B 1/0607; A61B 1/0615; A61B 1/0661; A61B 1/0669;
(Continued)

(56) References Cited

U.S. PATENT DOCUMENTS 5,695,505 A * 12/1997 Yoon ................. A61B 17/0487
606/151
6,799,065 B1 * 9/2004 Niemeyer .......... A61B 1/00149
600/407
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Larry E Waggle, Jr.
(74) *Attorney, Agent, or Firm* — Schwegman Lundberg & Woessner, P.A.

(57) ABSTRACT

A teleoperated surgical system is provided that comprises a support arm; a surgical instrument, moveably mounted to the support arm, including a housing a proximal end portion and a distal end portion and having an end effector at the distal end portion thereof; an actuator to impart movement to the surgical instrument; an optical fiber, including a proximal end portion and a distal end portion, mounted to the surgical instrument to emit first light from its distal end at the distal end portion of the surgical instrument; and a light source disposed to impart the first light to the proximal end of the optical fiber at a first angle within an acceptance angle of the optical fiber.

18 Claims, 13 Drawing Sheets

(51) Int. Cl.
  *A61B 1/06* (2006.01)
  *A61B 90/00* (2016.01)
  *G02B 23/24* (2006.01)
  *H04N 5/225* (2006.01)
  *A61B 34/20* (2016.01)

(52) U.S. Cl.
  CPC .......... *A61B 1/0615* (2013.01); *A61B 1/0661* (2013.01); *A61B 1/0669* (2013.01); *A61B 34/35* (2016.02); *A61B 90/06* (2016.02); *A61B 90/361* (2016.02); *G02B 23/2415* (2013.01); *H04N 5/2256* (2013.01); *A61B 2034/2065* (2016.02); *A61B 2090/061* (2016.02); *A61B 2090/062* (2016.02); *A61B 2090/306* (2016.02); *A61B 2090/309* (2016.02); *A61B 2090/371* (2016.02); *H04N 2005/2255* (2013.01)

(58) Field of Classification Search
  CPC .......... A61B 1/0676; A61B 2034/2065; A61B 34/35; A61B 90/06; A61B 2090/061; A61B 2090/062; A61B 90/10; A61B 90/30; A61B 2090/306; A61B 2090/309; A61B 90/36; A61B 90/361; G02B 23/2415; H04N 2005/2255; H04N 5/2256
  See application file for complete search history.

(56) References Cited

U.S. PATENT DOCUMENTS

| | | | |
|---|---|---|---|
| 7,992,573 B2* | 8/2011 | Wilson | A61B 5/061 128/899 |
| 8,527,094 B2* | 9/2013 | Kumar | A61B 34/37 700/259 |
| 8,892,191 B2* | 11/2014 | Brennan | A61B 5/0066 600/476 |
| 2012/0287403 A1* | 11/2012 | Music | A61B 90/30 351/221 |
| 2016/0187600 A1* | 6/2016 | Viering | A61B 1/00126 600/182 |

* cited by examiner

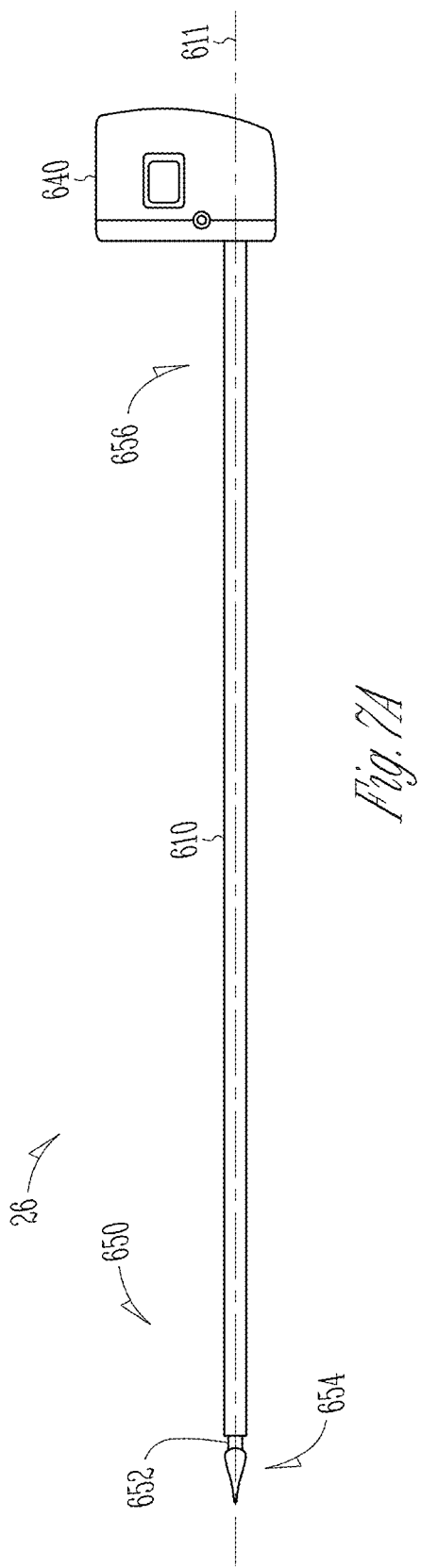
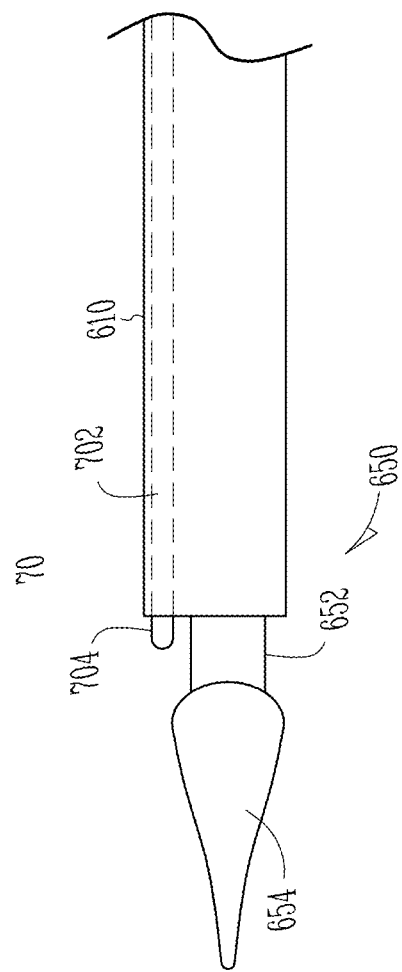
Fig. 7A
Fig. 7B

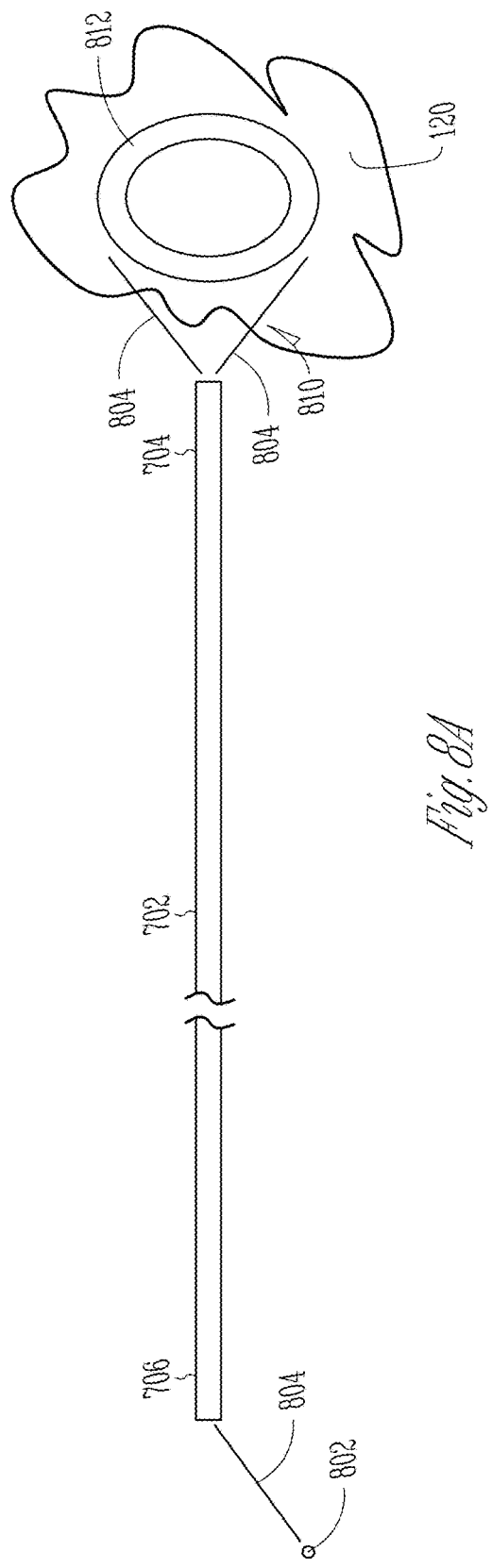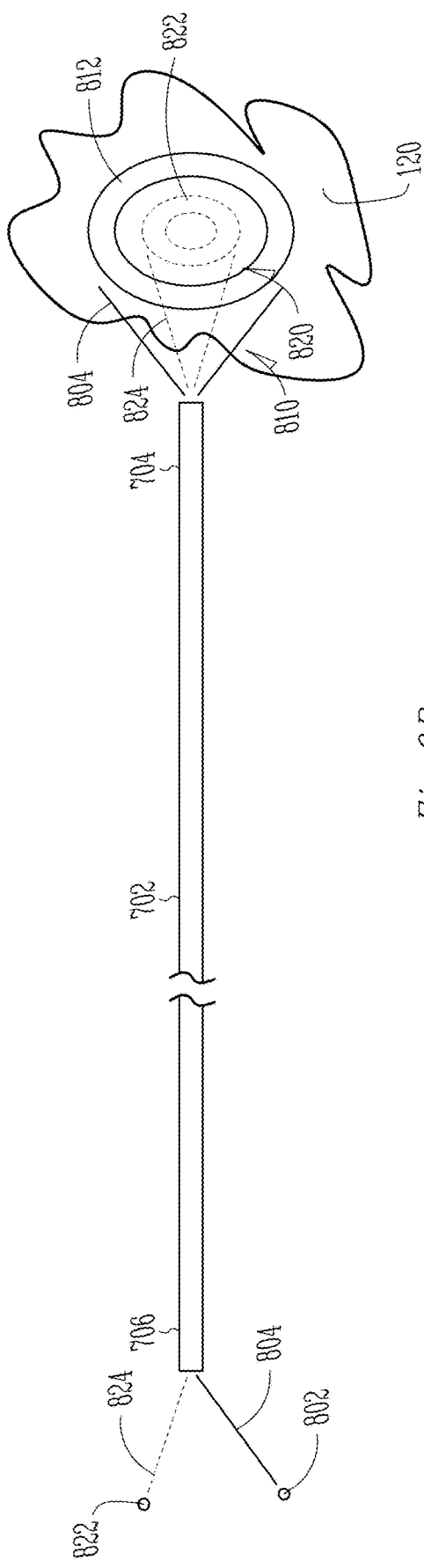

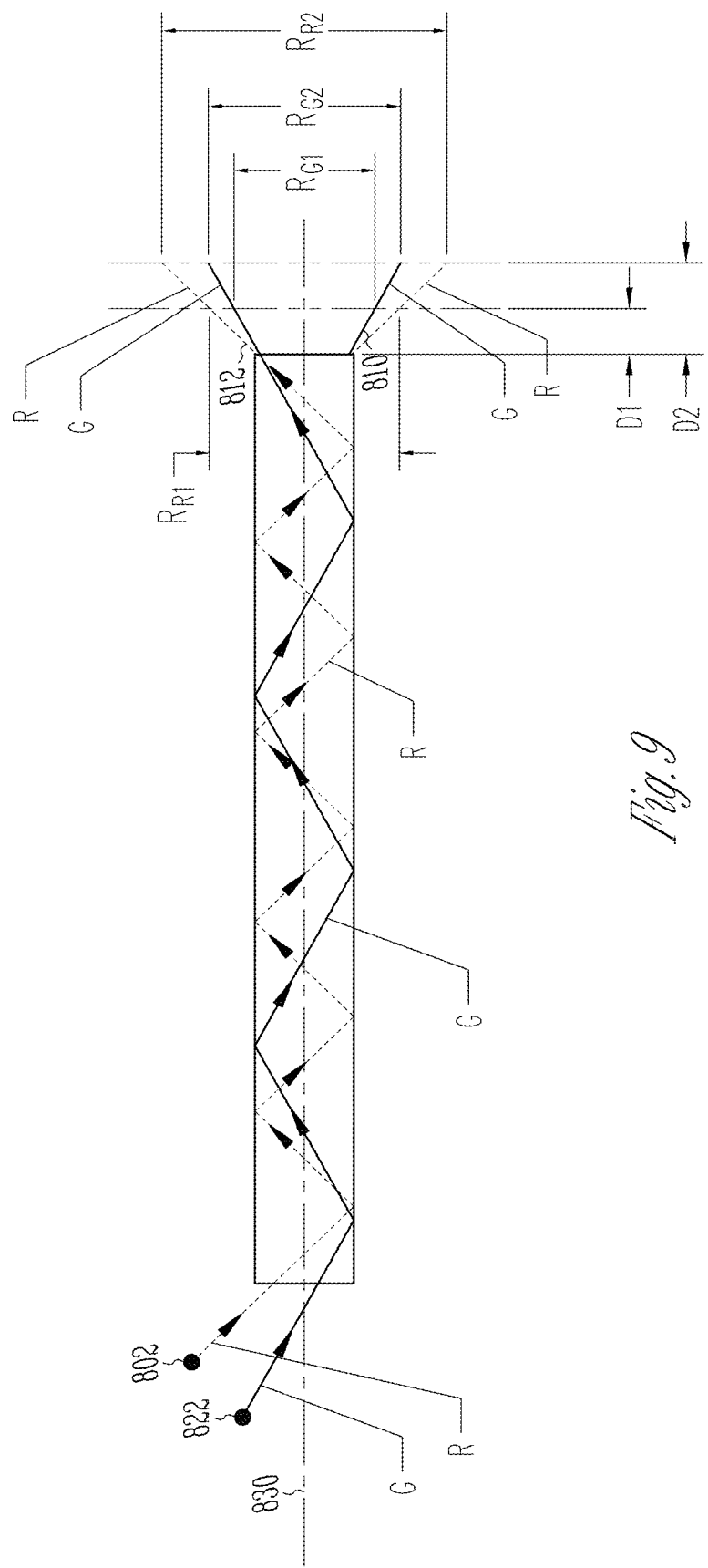

METHOD AND APPARATUS TO PROJECT LIGHT PATTERN TO DETERMINE DISTANCE IN A SURGICAL SCENE

CLAIM OF PRIORITY

This application claims the benefit of priority under 35 U.S.C. § 119(e) to U.S. Provisional Patent Application Ser. No. 62/551,677, filed on Aug. 29, 2017, which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. A stereoscopic endoscope may be inserted into a patient's body cavity to view a surgical scene during a minimally invasive surgical procedure. The surgical scene includes tissue structures and may include one or more surgical instruments inserted into the body cavity. Tissue and tool surface features may be difficult to visually discern due to uniform of tissue color or tissue smoothness, for example. Structured light has been used to discern contours and depth in a scene. However, space to project structured light is extremely limited within an endoscopic camera used to perform minimally invasive surgery.

SUMMARY

In one aspect, a teleoperated surgical system is provided that includes a support arm and a surgical instrument, moveably mounted to the support arm. The surgical instrument includes an elongated housing having a proximal end portion and a distal end portion and has an end effector at its distal end portion. An arm is provided to impart movement to the surgical instrument. An optical fiber is mounted to the surgical instrument to emit light from its first end. A light source is disposed to impart the light to the second end of the optical fiber at an angle within an acceptance angle of the optical fiber. Some instruments do not contain a wristed end effector and are like a rigid stick with an end effector at the distal section. Some endoscopic cameras are ridged in construction and do not have an end effector, they present as a continuous rigid device.

In another aspect, a method is provided to control movement of a surgical instrument in a teleoperated surgical system. Light is imparted to a proximal end of an optical fiber, mounted to the surgical instrument, at a first angle within an acceptance angle of the optical fiber. The light is transmitted within the optical fiber from the proximal end portion of the optical fiber to a distal end portion of the optical fiber. The light is emitted at the distal end of the optical fiber, in a circular conical pattern to produce the circular pattern incident upon the object. A stereographic view of an object having a circular light pattern incident thereon is provided. User input is received to adjust position of the surgical instrument and the optical fiber mounted thereon, to thereby adjust size of the circular light pattern incident upon the object.

In another aspect, a method is provided to control movement of a surgical instrument in a teleoperated surgical system. A tissue surface depth map is produced for a tissue surface within a field of view of a stereoscopic viewing system. A surgical instrument is moved within the field of view to change its position in relation to the tissue surface. A circular conical pattern of light is projected, from an optical fiber mounted on the surgical instrument, onto an area of the tissue surface the area comprising at least two locations. A distance between the instrument and the tissue surface at the at least two distances is determined by matching pixels in left and right sensors of the stereoscopic viewing system illuminated by light reflected from the circular conical pattern of light with locations within the tissue surface depth map and determining a size dimension of the projected circular conical light pattern incident upon the tissue surface at the at least two positions.

BRIEF DESCRIPTION OF THE DRAWINGS

Certain embodiments are illustrated by way of example and not limitation in the figures of the accompanying drawings.

FIG. 7A is a side view of a surgical instrument, which includes an elongated tubular shaft having a centerline longitudinal axis, a distal portion for insertion into a patient's body cavity and proximal portion coupled adjacent a control mechanism.

FIG. 7B is an enlarged view of the distal portion of the surgical instrument, shown partially in cut-away, having an optical fiber mounted thereon.

FIG. 8A is an illustrative drawing showing a first light source injecting light to a proximal end of an optical fiber resulting in a circular cone pattern light emanating from a distal end the fiber.

FIG. 8B is an illustrative drawing showing first and second light sources injecting light to the proximal end of an optical fiber at different angles resulting in concentric circular cones of light emanating from a distal end of the fiber.

FIG. 9 is an illustrative cross-section view of the optical fiber of FIGS. 8A-8B showing internal reflections of the light from first and second light sources positioned to inject light at different angles.

DESCRIPTION OF EMBODIMENTS

Minimally Invasive Surgical System

Figure 1:
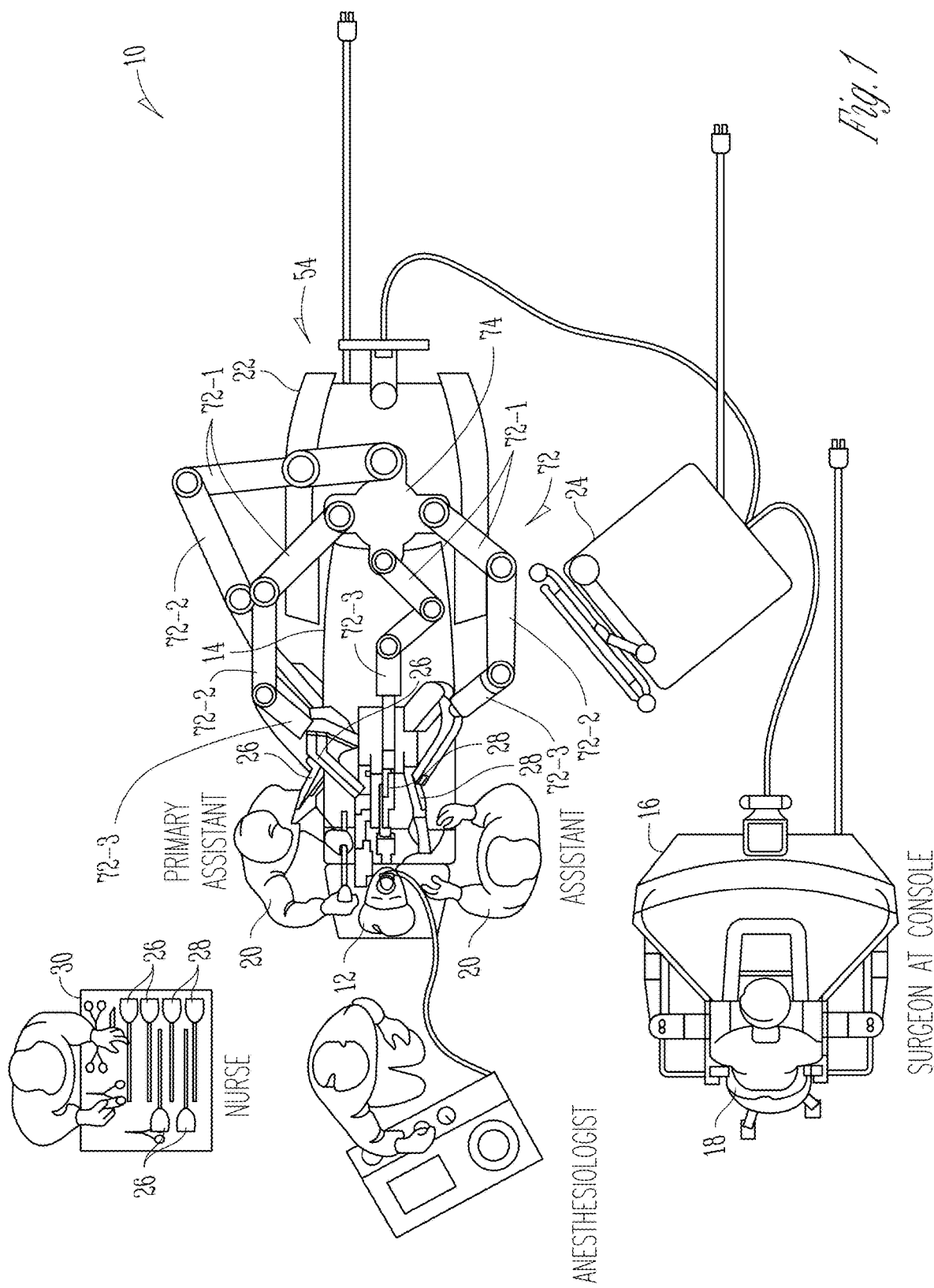
FIG. 1 is a plan view of a minimally invasive teleoperated surgical system.

FIG. 1 is a plan view of a minimally invasive teleoperated surgical system 10, typically used for performing a minimally invasive diagnostic or surgical procedure on a patient 12 who is lying on a mobile operating table 14. The system includes a mobile surgeon's console 16 for use by a surgeon 18 during the procedure. One or more surgical team members 20 may also participate in the procedure. The minimally invasive teleoperated surgical system 10 further includes a mobile patient-side cart 22 and a mobile electronics cart 24. In some embodiments, the table 14, surgeon's console 16, patient-side cart 22, and the electronics cart 24.

The patient-side cart 22 includes multiple segmented mechanical support arms 72, each having one end portion rotatably mounted to a vertical support structure 74 and having another end mounting a removably coupled surgical instrument 26. In some of embodiments, each mechanical support arm 72 includes a first segment 72-1, a second segment 72-2 and a third segment 72-3. During setup for a surgical procedure, the multiple segments of at least one support arm 72 are moved to position a surgical instrument for insertion within a minimally invasive incision in the body of the patient 12. During the surgical procedure, while surgical instruments are inserted within a patient's body cavity, the surgeon 18 views the surgical site through the surgeon's console 16. An image of the surgical site can be obtained by an endoscope 28, such as a stereoscopic endoscope, which a surgeon can manipulate at the patient-side cart 22 to orient the endoscope 28. Computer processors located on the electronics cart 24 can be used to process the images of the surgical site for subsequent display to the surgeon 18 through the surgeon's console 16. The number of surgical instruments 26 used at one time will generally depend on the diagnostic or surgical procedure.

Figure 2:
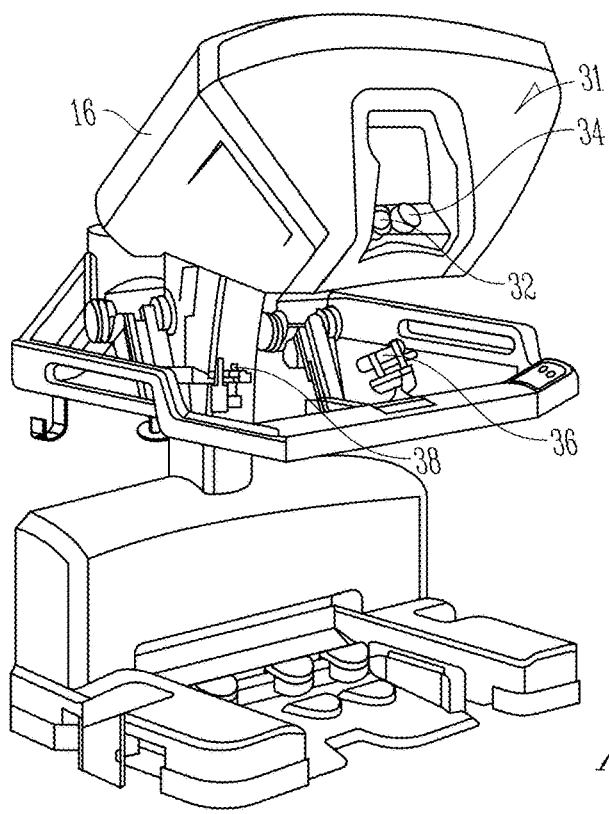
FIG. 2 is a perspective view of a surgeon's console.

FIG. 2 is a perspective view of the surgeon's console 16. The surgeon's console 16 includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36.

Figure 3:
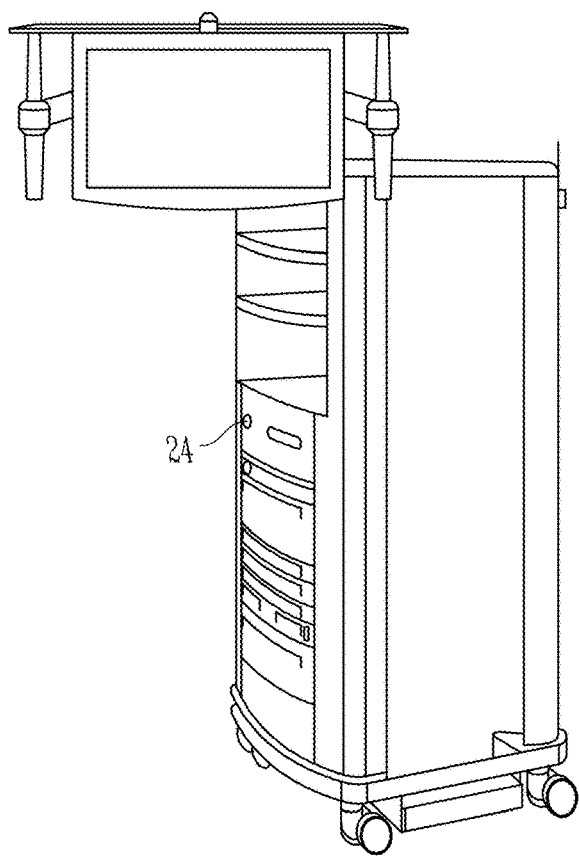
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
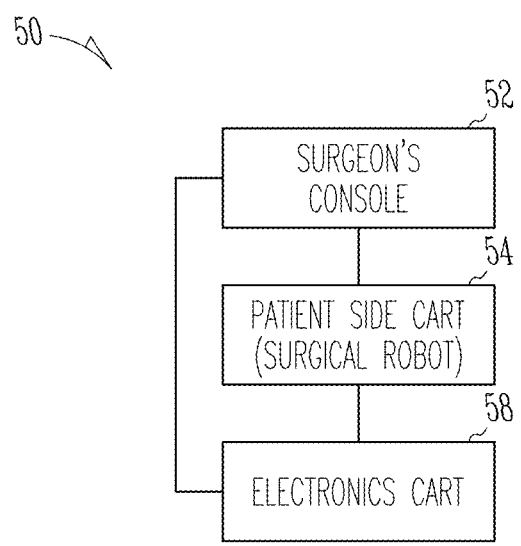
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patient-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Figure 5:
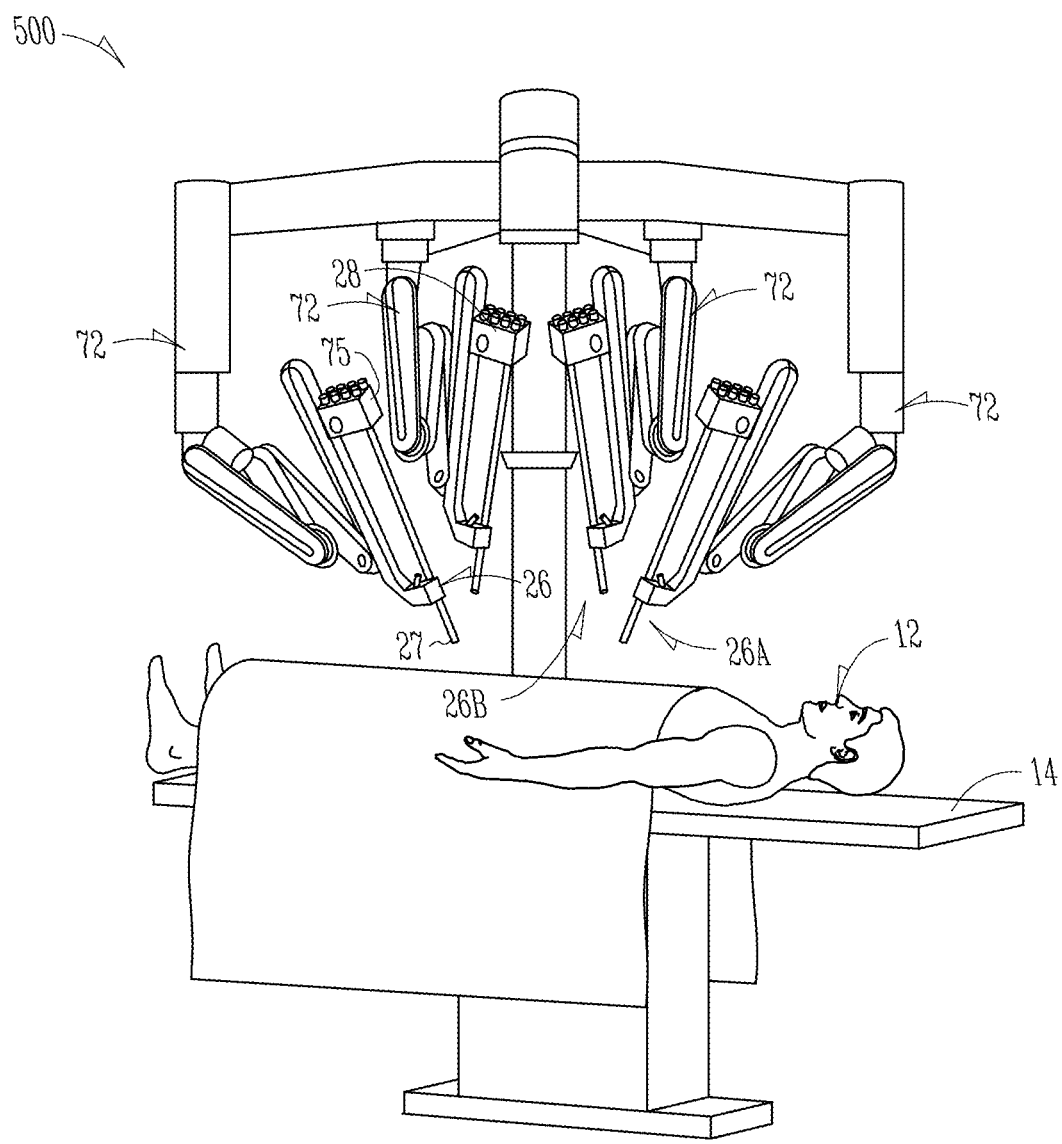
FIG. 5 is a perspective view of a patient-side cart of a minimally invasive teleoperated surgical system, in accordance with embodiments.

FIG. 5 is a perspective view of a patient-side cart 54 of a minimally invasive teleoperated surgical system 10, in accordance with embodiments. The patient-side cart 54 includes four mechanical support arms 72. A surgical instrument manipulator 73, which includes motors to control instrument motion, is mounted at the end of each support arm assembly 72. Additionally, each support arm 72 can optionally include one or more setup joints (e.g., unpowered and/or lockable) that are used to position the attached surgical instrument manipulator 73 in relation to the patient for surgery. While the patient-side cart 54 is shown as including four surgical instrument manipulators 73, more or fewer surgical instrument manipulators 73 may be used.

A functional teleoperated surgical system will generally include a vision system portion that enables a user of the teleoperated surgical system to view the surgical site from outside the patient's body 12. The vision system typically includes a endoscopic camera instrument 28 for capturing video images and one or more video displays for displaying the captured video images. In some surgical system configurations, the endoscopic camera 28 includes optics that transfer the images from a distal end of the endoscopic camera 28 to one or more imaging sensors (e.g., CCD or CMOS sensors) outside of the patient's body 12. Alternatively, the imaging sensor(s) can be positioned at the distal end of the endoscopic camera 28, and the signals produced by the sensor(s) can be transmitted along a lead or wirelessly for processing and display on the one or more video displays.

Referring to FIG. 5, in one aspect, for example, an individual surgical instrument 26 and a cannula 27 are removably coupled to manipulator 73, with the surgical instrument 26 inserted through the cannula 27. One or more teleoperated actuators of the manipulator 73 move the surgical instrument 26 as a whole. The manipulator 73 further includes an instrument carriage 75. The surgical instrument 26 is detachably connected to the instrument carriage 75. In one aspect, the instrument carriage 75 houses one or more teleoperated actuators inside that provide a number of controller motions that the surgical instrument 26 translates into a variety of movements of an end effector on the surgical instrument 26. Thus, the teleoperated actuators in the instrument carriage 75 move only one or more components of the surgical instrument 26 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In an alternate embodiment, instrument carriage 75 does not house teleoperated actuators. Teleoperated actuators that enable the variety of movements of the end effector of the surgical instrument 26 are housed in a location remote from the instrument carriage 75, e.g., elsewhere on patient-side cart 54. A cable-based force transmission mechanism or the like is used to transfer the motions of each of the remotely located teleoperated actuators to a corresponding instrument-interfacing actuator output located on instrument carriage 75. In some embodiments, the surgical instrument 26 is mechanically coupled to a first actuator, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of jaws of an end effector, for example.

Figure 6:
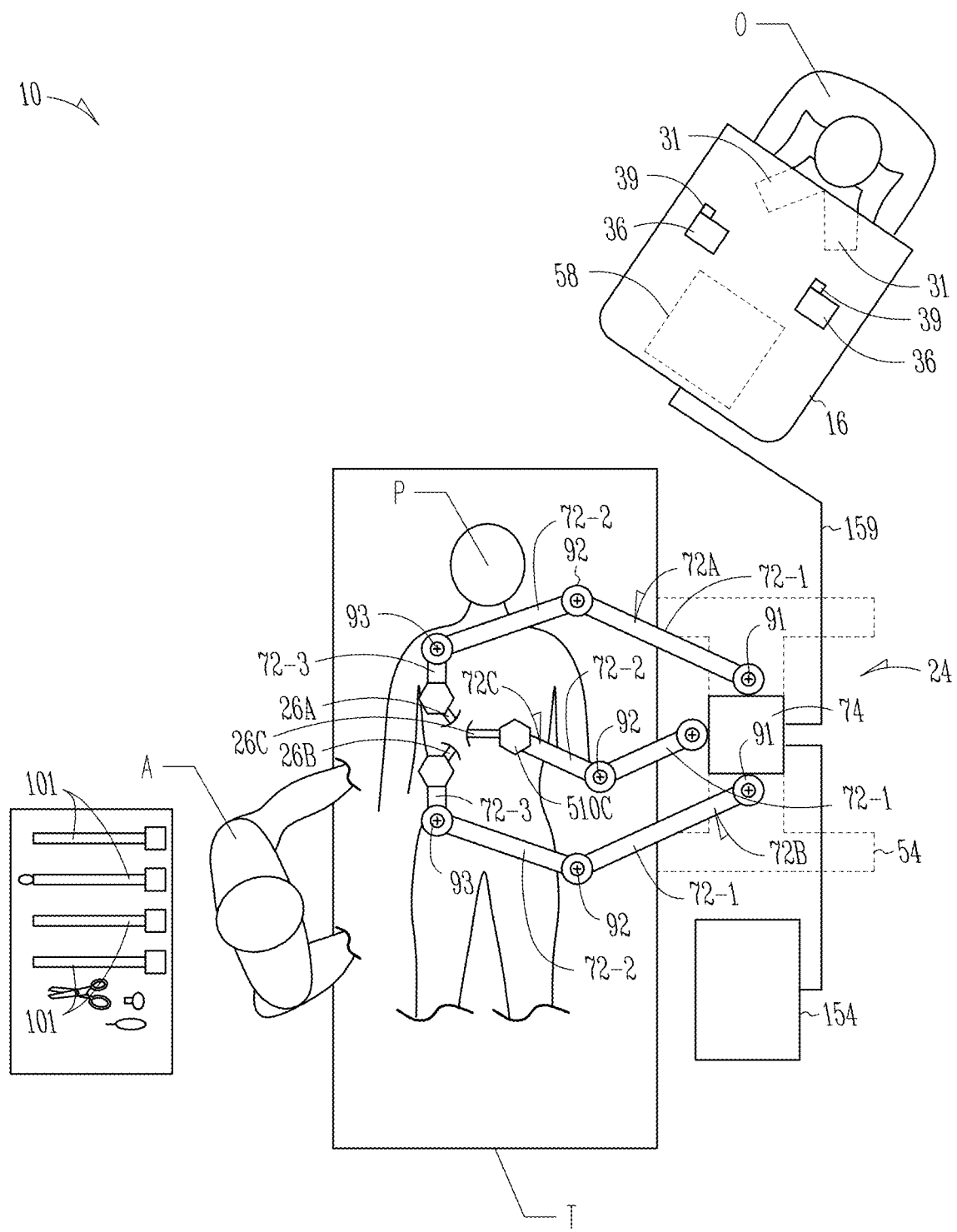
FIG. 6 is an illustrative simplified block diagram showing an example positioning of mechanical support arms of the teleoperation surgery system during a surgical procedure in accordance with some embodiments.

FIG. 6A is an illustrative simplified block diagram showing an example positioning of mechanical support arms 72A-72C of the teleoperation surgery system 10 during a surgical procedure in accordance with some embodiments. In some embodiments, the patient-side system 54 includes at least three mechanical support arms 72A-72C. In some embodiments, each of the mechanical support arms 72A-72C includes rotatably mounted first, second and third segments 72-1, 72-2 and 72-3. A center-located mechanical support arm 72 may support an endoscopic camera 28 suitable for capture of images within a field of view of the camera. The mechanical support arms 72 to the left and right of center may support surgical instruments 26A and 26B, respectively, which may manipulate anatomical tissue. During setup for a surgical procedure, the support arm segments are pre-positioned to support endoscope and instruments in precise position and orientation to for robot assisted manipulation by a surgeon to perform a medical procedure.

A user or operator O (generally a surgeon) performs a surgical procedure on patient P by manipulating control input devices 36, such as hand grips and foot pedals at a master control console 16. The operator can view video frames of images of a surgical site inside a patient's body through a stereo display viewer 31. A computer processor 58 of the console 16 directs movement of teleoperationally controlled instruments 26, 26A-26B and 28 via control lines 159, effecting movement of the instruments using a patient-side system 24 (also referred to as a patient-side cart).

Surgical Instrument

FIG. 7A is a side view of a surgical instrument 26, which includes an elongated tubular shaft 610 having a centerline longitudinal axis 611, a distal (first) portion 650 for insertion into a patient's body cavity and proximal (second) portion 656 coupled adjacent a control mechanism 640. The surgical instrument 26 is used to carry out surgical or diagnostic procedures. The distal portion 650 of the surgical instrument 26 can provide any of a variety of end effectors 654, such as the forceps shown, a needle driver, a cautery device, a cutting tool, an imaging device (e.g., an endoscope or ultrasound probe), or the like. The surgical end effector 654 can include one or more functional mechanical degrees of freedom, such as jaws that open or close, or a knife that translates along a path; multiple degree of freedom end effectors include devices such as staplers or vessel sealers where there are both jaws and various other mechanisms so the tool can perform the required surgical task. In the embodiment shown, the end effector 654 is coupled to the elongate tube 610 by a wrist 652 that allows the end effector to be oriented relative to the elongate tube centerline axis 611. The wristed portion may afford one or more degrees of freedom. The control mechanism controls movement of the overall instrument, wrist, and the end effector at its distal portion.

FIG. 7B is an enlarged view of the distal portion 650 of the surgical instrument 26, shown partially in cut-away, having an optical fiber 702 mounted thereon. The optical fiber 702 extends between a proximal end portion 656 and a distal end portion 650 of the surgical instrument 26. A proximal (second) end portion 706 (no shown) of the optical fiber 704 is disposed to receive light from a light source (not shown). A distal (first) end portion 706 of the optical fiber 702 is disposed to project light transmitted within the fiber from the light source in a direction largely parallel to the centerline axis 611 of the surgical instrument 26. The fiber 702 may be routed through the wrist of the tool if desired. The fiber 702 may be incorporated into the jaws of the instrument and proceed through the wrist and out to the most distal part of the instrument.

Light Source and Optical Fiber Configured to Project a Light Pattern

FIG. 8A is an illustrative drawing showing a first light source 802 injecting light to a proximal end 706 of the optical fiber 702 of FIG. 7B resulting in a circular cone pattern light 810 emanating from a distal end 704 the fiber 702. More specifically, the first light source 802 provides first light 802 having a first wavelength to a proximal end 706 of a multimodal optical fiber 702. The first light 804 emanates from a distal end 704 of the optical fiber 702 in a first circular cone pattern 810. The first light source 802 may be comprised of one or more light emitting diodes (LEDs) (or an array of LEDs that are a single device), or a laser. The first light source 802 is positioned to inject light to the proximal end 706 of the fiber 702 at an angle that is within an acceptance angle of the fiber. The optical fiber 702 may have a diameter in a range 30-200 microns, for example. The light 804 injected by the first light source 802 entering the optical fiber within the acceptance angle, over some distance such as 30 cm for example, fills that angular mode of the fiber. The first light 804 exits the distal end 704 of the optical fiber 702 at the same angle that it entered. The optical fiber 702 is rotationally symmetric and the distal end 704 of the fiber 702 is terminated and polished flat such that the injected light from the first light source 802 exits in the first circular cone pattern 810. The first circular cone of light incident when upon a tissue surface 120 in front of a surgical instrument 26 on which the optical fiber 702 is mounted has the appearance of a halo or ring of light 812. An optical element or elements may be located between source 802 and fiber entrance 706; such an optical system would increase the proportion of the light from source 802 that enters the fiber at 706. The optical system also affords flexibility in the entry angles for the light into fiber 706 from the source 802.

FIG. 8B is an illustrative drawing showing first and second light sources 802, 822 injecting light to the proximal end 706 of an optical fiber 702 of FIG. 7B at different angles resulting in concentric circular cones of light emanating from a distal end 704 of the fiber 702. More specifically, the first light source 802 provides first light 804 having a first wavelength to the proximal end 706 of the optical fiber 702, and the second light source 822 provides second light 824 having a second wavelength to the proximal end 706 of the optical fiber 808. First and second light 804, 824 emanate from the distal end 704 of the optical fiber 808 in first and second concentric circular cone patterns 810, 820. The second cone pattern 820 has a smaller diameter than the first cone pattern 810. The first light source 802 is positioned to inject first light 804 to the proximal end 706 of the fiber 702 at the first angle that is within the acceptance angle of the fiber. The second light source 822 is positioned to inject the second light 824 to the proximal end 706 of the fiber 808 at a second angle, steeper than the first angle, that is within the acceptance angle of the fiber 808. The first and second light 804, 824 injected to the proximal end 706 of the fiber 702 at respective first and second angles from the first and second light sources 802, 822 emerges as first and second concentric cones of light 810, 820, at the respective first and second angles at which they were injected. In other words, each cone of light that exits the distal end 704 of the fiber 702 has an angle that matches the angle of incidence at which it entered at the proximal end 706 of the fiber 702. The light of these multiple cones when incident upon a tissue surface 120 such as anatomical tissue, has the appearance of concentric anuluses of light with a gaussian crossectional profile 812, 822. The different light sources may produce light having different wavelengths (i.e. colors) such that the concentric rings can be superimposed one about the other, a red ring surrounding a green ring for example, to increase the saliency of the light. Also note that one can create patterns with more than one ring at any point in time by turning on multiple light sources, of which 802 and 822 are illustrative. For example, the light source could be a linear array of small LED sources and between the array and the fiber an optical system by be inserted to better couple the light from the LEDs to the fiber. Additionally, the LED array may be fabricated on flex so the array may be curved to improve the performance and simplicity of the coupling optics. Also note that the array need not have each LED in a line, they merely need to appear at the correct angle from the fiber's point of view. This is illustrated by sources 802 and 822 which are located on opposite sides of the centerline of the fiber and at different distances. In such an implementation, the output of the fiber may be a series of rings and that series of rings may be controlled in any number of ways and can thus afford the ability to create ring patterns that facilitate the determination of depth.

In some embodiments a first and/or second light sources 802, 822 may produce pulsating or cycled on and off or modulated in time to increase visibility of light incident upon a tissue surface. An advantage of injecting light at an offset angle to generate a ring pattern is its simplicity in that no special processing or handling of the optical fiber is required. The fiber 702 may be the same type as the fiber used in an illumination path of an endoscopes, for example; or it may be of a larger or smaller diameter.

FIG. 9 is an illustrative cross-section view of the optical fiber 702 of FIGS. 8A-8B showing internal reflections of the light from first and second light sources 802, 822 positioned to inject light at different angles. The first light source 802 produces light at a first wavelength such as green (G). The first light source is positioned to be longitudinally offset from the proximal end 706 of the fiber 702 and to be offset at a radial distance from a center longitudinal axis 830 of the optical fiber core such light at the first wavelength enters the proximal end 706 of the fiber 702 at the first angle. The second light source 822 produces light at a second wavelength such as red (R). The second light source 822 is positioned to be longitudinally offset from the proximal end 706 of the fiber 702 and to be offset at a radial distance from the center longitudinal axis 830 of the optical fiber core such light at the second wavelength enters the proximal end 706 of the fiber 702 at the second angle, steeper than the first angle. First light (G) from the first light source 802 and second light (R) from the second light source 822 propagate within the fiber 702 through internal reflection and exit at the distal end 704 of the fiber 702 at the same angles that they entered the fiber. Thus, the first light (G) exits at a shallower angle than the second light (R). As a result, a first annular cone 810 having the first wavelength (G) spreads out more gradually with distance than a second annular cone 812 having the second wavelength (R). For example, at a first longitudinal distance $D_1$ from the distal end 704 of the fiber, the first cone 810 has spread to a radius $R_{G1}$ and the second cone 812 has spread to a larger radius $R_{R1}$, and at a second longitudinal distance $D_2$ from the distal end 704 of the fiber, the first cone 810 has spread to a larger radius $R_{G2}$ and the second cone 812 has spread to an even larger radius $R_{R2}$. It will be appreciated that since the diameter of a cone of light increases with increasing distance from the distal end of the fiber 702, a diameter of the cycle of light incident upon a tissue surface provides an indication of distance between the first surgical instrument, upon which the fiber is disposed, and the tissue surface. Thus, a surgeon may view the size of the circular light pattern to visually estimate distance between the first surgical instrument and the tissue surface. Additionally, vision processing software may perform the same task and estimate the distance algorithmically.

Figure 10A:
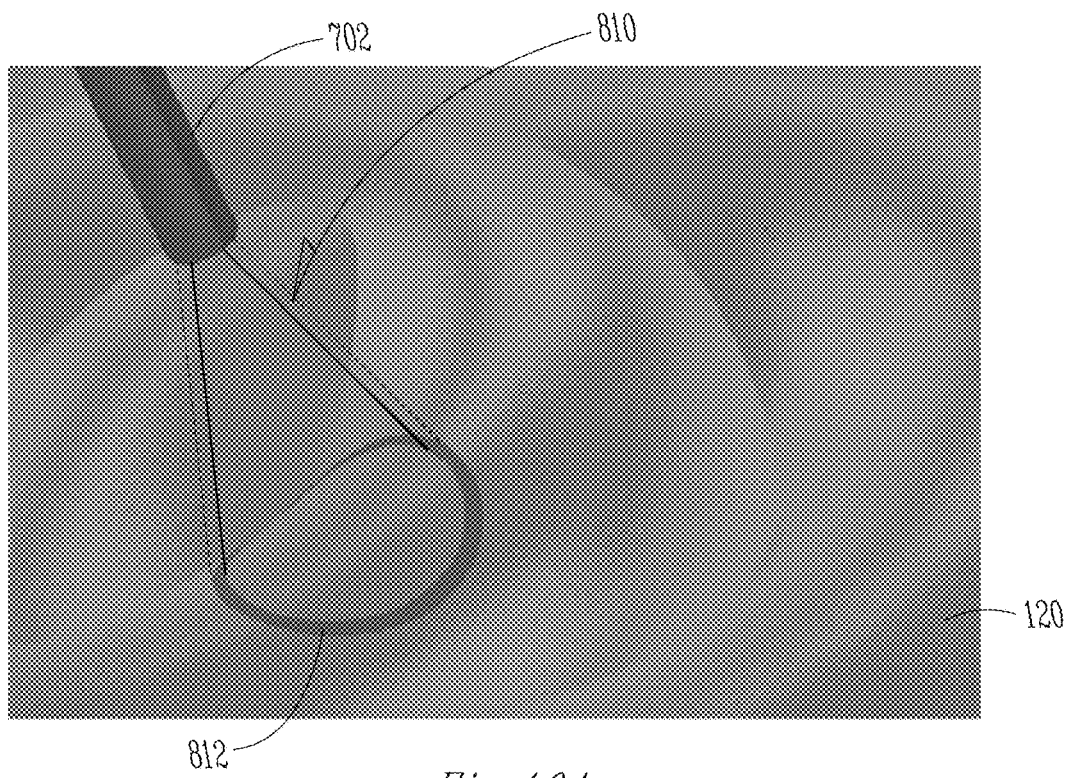
FIGS. 10A-10B are illustrative first and second illustrative views of the first circular cone pattern of light incident upon a tissue at a surgical site from two different endoscope viewpoints.
Figure 10B:
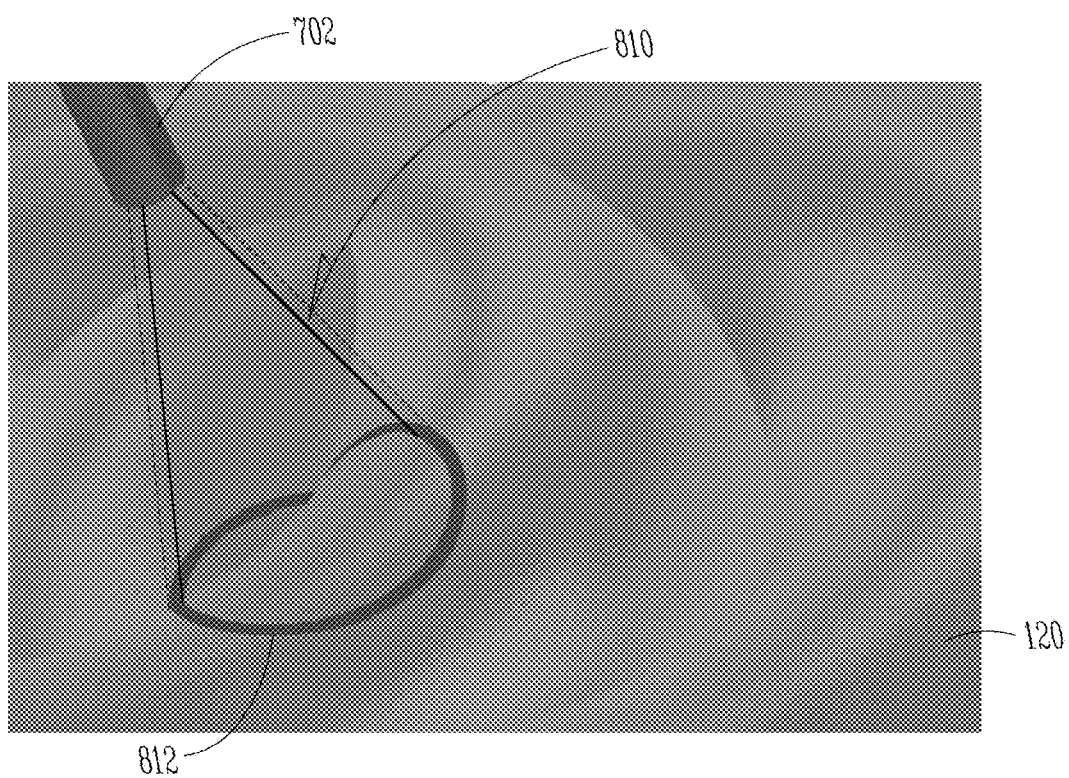

Example—Adjustment of Endoscope Based Light Pattern Incident Upon Tissue Surface FIGS. 10A-10B are illustrative first and second illustrative views of the first circular cone pattern 810 of light incident upon a tissue 120 at a surgical site from two different endoscope viewpoints. The position of the endoscope (not shown) may be changed to change its view of the surgical scene. The tissue surface contor 120 includes ridges and valleys. It will be appreciated that a visual appearance of the incident circular light pattern 812 may appear distorted due its falling upon uneven three-dimensional tissue surface structures thereby providing an indication to a surgical team of shape of the tissue surface. For example, the appearance of the circular cone of light is different in FIGS. 10A-10B due to the different endoscope positions corresponding to the different views. Moreover, in the illustrative views of FIGS. 10A-10B, portions of the cone of light incident upon surface regions on the far side of a tissue ridge is hidden behind the ridge and not visible to the endoscope.

Example—Projected Light Pattern to Automatically Predict Contact and Distance

Figure 11:
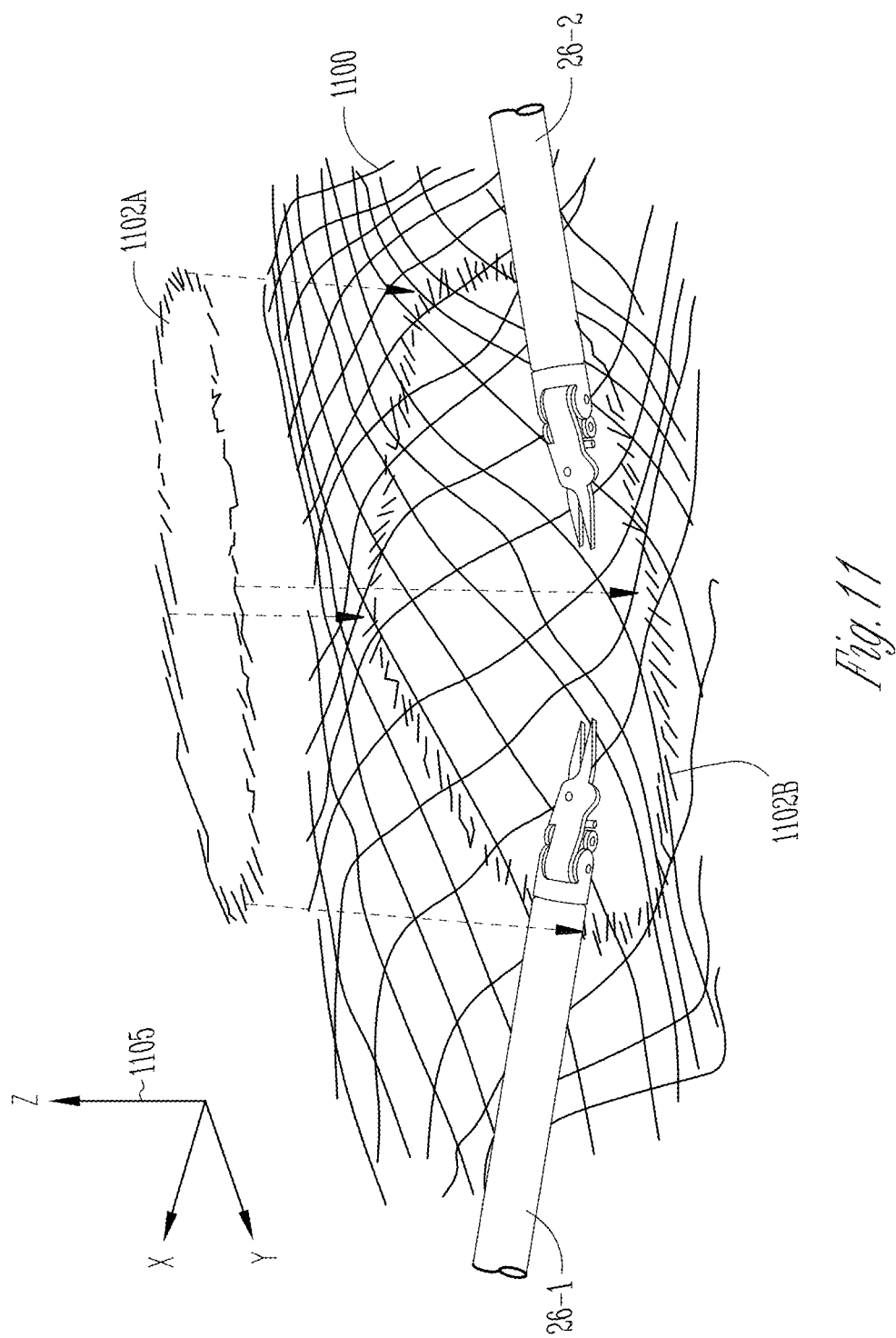
FIG. 11 is an illustrative drawing representing a perspective view of a tissue structure image is overlaid with a tissue surface depth map.

FIG. 11 is an illustrative drawing representing a perspective view of a tissue structure image 1102A is overlaid with a tissue surface depth map 1100. The location of tissue surface features may be captured within camera images of both cameras of a stereo imaging system may be used to calculate the distances from the stereo endoscope to the tissue surface features and with enough features, a three-dimensional depth map of the tissue surface may be computed for the scene. U.S. Pat. No. 8,147,503 (Zhao et el.), which is expressly incorporated herein in its entirety by this reference, describes a stereographic imaging system feature matching processes that may be used to produce a tissue surface depth map. In some embodiments, a structured light pattern may be used to produce a three-dimensional tissue surface depth map using light spot patterns or sinusidal light patterns, for example, as described in commonly assigned U.S. Provisional Application No. (ISRG09900), which is expressly incorporated herein in its entirety by this reference. In some embodiments, a pre-scanned image 1102A (for example, CT images) may be aligned to a stereographic camera coordinate system 1605 and then overlaid as an overlaid image 1102B onto a surface map or depth map 1100 of the tissue surface.

A depth map may provide to the surgical system information about tissue surface contours or about tissue distance from a surgical tool at a surgical site that may not be readily visible to a surgeon viewing the scene through a stereoscopic viewer and camera system. For example, contours of a tissue surface having a smooth texture or substantially uniform coloration may be difficult to visually discern through an stereoscopic endoscope, for example. A depth map can fill in tissue surface depth information that is difficult to visually discern.

In accordance with some embodiments, a current position and pose of an stereo endoscope 28 incorporated within a teleoperated surgical system may be known based upon the position and pose of a robotic support arm 72 on which it is mounted. An approximate position and pose of a surgical instrument 26 also may be known based upon position and pose of a robotic support arm 26 on which it is mounted. A tissue surface map geometry may be placed in a coordinate system of the surgical system 1105 so that a coordinate transformation between additional tools and robotic support arms of the surgical system may be calculated with respect to the stereographic endoscope and thus a tissue surface depth map.

A first surgical instrument 26-1 includes an optical fiber 702 configured to project a circular conical light pattern onto surface structures at a surgical site. The optical fiber 702 emits a light pattern that is separable, and therefore identifiable, from a stereographic image of the surgical scene viewed by the surgical team. In some embodiments, the structured light pattern includes an annular hollow cone of light. The annular light pattern incident upon the tissue surface has a size dimension, such as a diameter, which is indicative of distance of the optical fiber from the tissue surface. As explained with reference to FIG. 9, a size dimension of a circular conical light pattern is proportional to the distance from a distal end of the optical fiber. Thus, an estimate of distance between the distal end of an optical fiber that emits a conical light pattern and a tissue surface on which the conical light pattern is incident upon may be determined based upon a size dimension (e.g., diameter) of the incident light pattern upon the tissue surface. The pattern of pixels illuminated in the stereoscopic imaging sensors can be used to infer the diameter or size dimension of the incident light pattern so knowing the cone angle allows the distance calculation. In some embodiments, the structured light source includes a wavelength range (e.g., NIR or short wavelength blue for example) that is not used in the visible image acquisition. In some embodiments, for example, the light source projects the pattern with an intensity that changes with time and is thus recoverable from the background illumination by adding when the pattern is on and subtracting when it is off. In some embodiments, for example, a modulation enhancement technique may be used to separate the pattern to recover a faint modulated signal from video that is capturing a white light image, such as described by, M. A. Elgharib et al., Video Magnification in Presence of Large Motions, *IEEE Conf. on Computer Vision and Pattern Recognition (CVPR)*, 2015; and Hao-Yu Wu et al., Eulerian Video Magnification for Revealing Subtle Changes in the World, *ACM Transactions on Graphics, Volume* 31, *Number* 4 (*Proc. SIGGRAPH*), 2012, for example.

Figure 12:
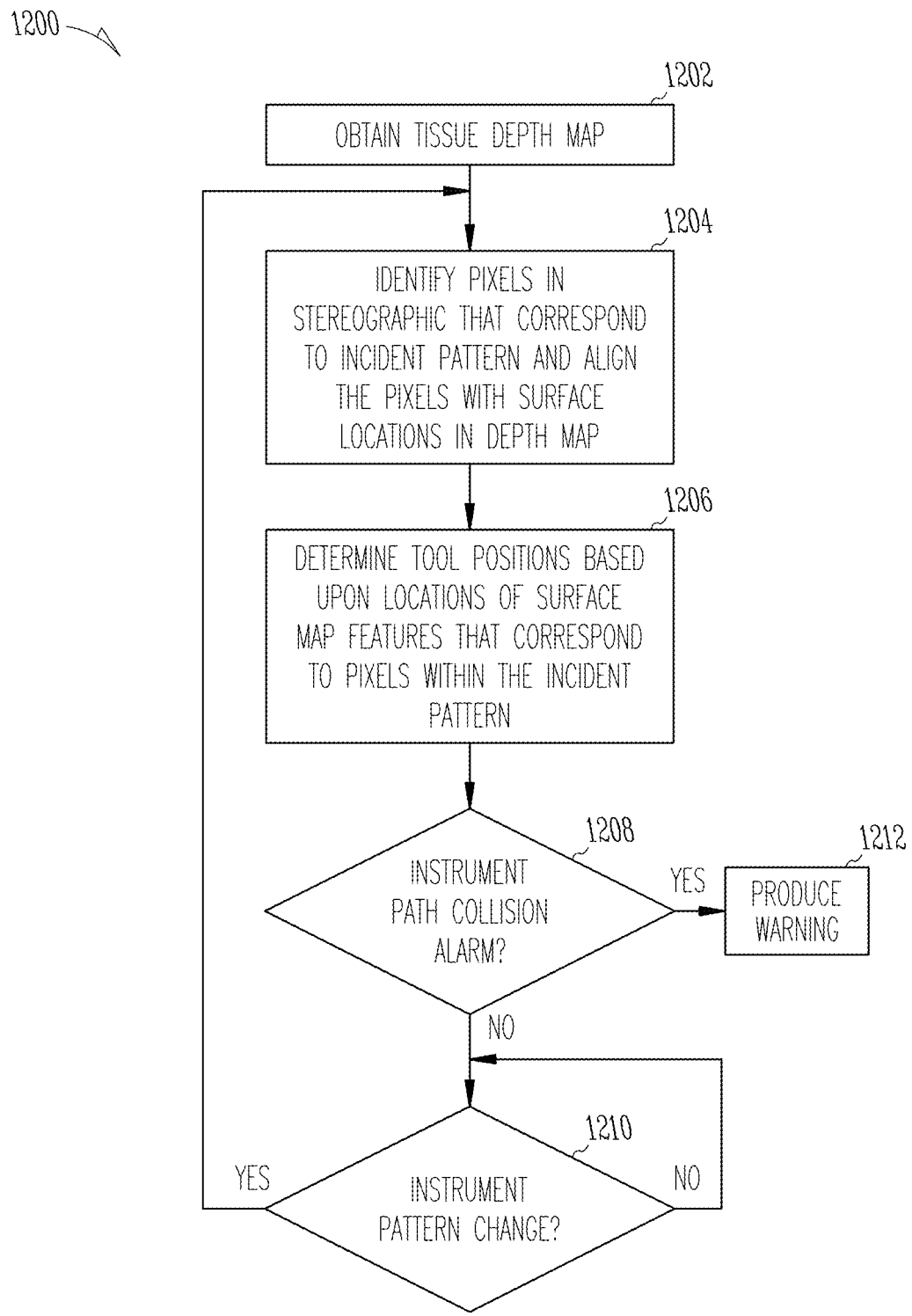
FIG. 12 is an illustrative flow diagram representing a process to use a tissue surface depth map to determine position of a surgical tool based upon a light pattern projected from the tool position within a surgical scene.

FIG. 12 is an illustrative flow diagram 1200 representing a process to use a tissue surface depth map 1100 to determine position of a surgical tool 26-2 based upon a light pattern projected from the tool position within a surgical scene. At block 1202, a surface depth map is determined. At block 1204, a processor associated with the stereographic imaging system identifies pixels in the stereographic image that are associated with the identified pattern and associates these pixels with surface locations in the tissue surface depth map. At block 1206, surface depth map locations of the pixels associated with the identified pattern are used to determine position and pose of the first tool relative to the camera through geometric calculation or by an optimization method or machine learning. In some embodiments the processor may be configured to perform a machine learning process that is presented with many real or simulated example cases of images and known distances to predict the position of the first tool.

Decision block 1208 determines whether a sequence of positions of the surgical tool 26-1 indicate that it is on a collision course with a tissue surface and whether it is close enough to produce a warning alarm. Decision block 1210 determines whether the tool 26-1 has moved and if so, control is returned to blocks 1204 and 1206 to determine a next incremental position of the first tool. Movement detection may be made based upon a change in the pixels of the stenographic image on which the pattern is incident. The iteration of blocks 1210, 1204, 1206 in response to detected movement of the tool 26-1 provides a basis to estimate path of the tool 26-1, which may be used by decision block 1208 to predict when further incremental movement of the first tool will result in contact between the first tool and the tissue surface, which is represented by the tissue depth map. More specifically, following the initial position and normal vector determination, the first tool 26-1 may be moved by a surgeon, for example, incrementally closer to a tissue surface. The pose and position of the first tool 26-1 at a succession of positions incrementally closer to a tissue surface may be determined based upon the changing light patterns projected onto the tissue surface that are captured by the stereo endoscope 28. The process of determination of incremental changes in position of the first tool 26-1 repeats to identify a sequence of first tool positions that collectively provide a running estimate of the trajectory of the first tool. Based upon the estimated trajectory of the first tool a next incremental position of the first tool on its trajectory is predicted. Such prediction may be used by decision block 1208 as a basis to provide an alert at block 1212 to a user of a manually controlled first tool in advance of a predicted contact between tool and tissue surface, for example. Such alert may include generating a blinking light image within a stereographic image of a surgical scene, for example. This approach enables the position of the tool to be determined from the image being seen, rather than from the kinematics of the robotic arm holding the tool. This enables some degree of independent sensor verification, and may obviate the need to know the relative absolute coordinate systems of the reference points for the arm holding the tool and the arm holding the endoscope.

Example—Projected Light Pattern to Guide a Path of a Tool at a Surgical Site

Figure 13A:
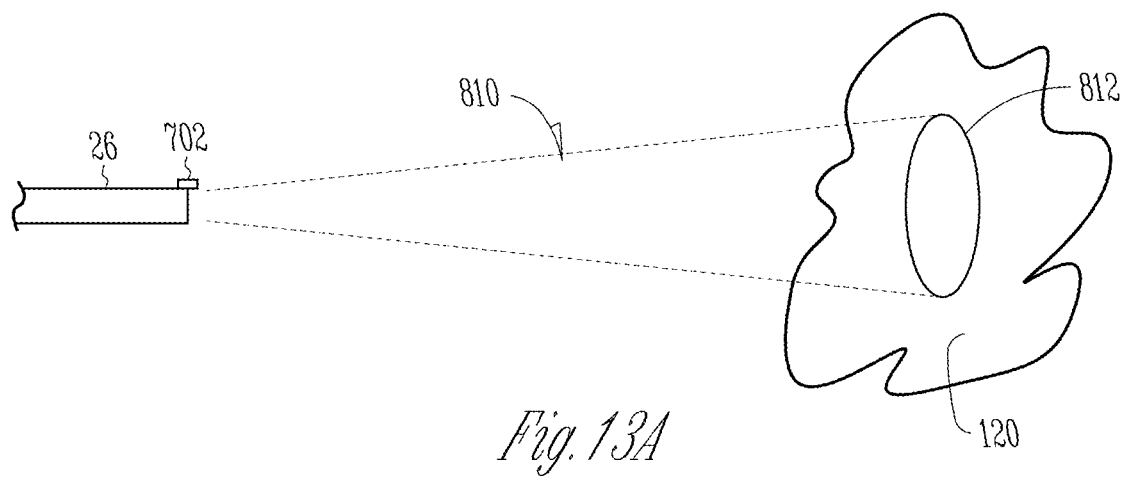
FIGS. 13A-13C are illustrative drawings to represent that a diameter size dimension of projected circular conical light pattern incident upon a tissue surface in the path of surgical instrument provides an indication of distance between the instrument and the tissue surface.
Figure 13B:
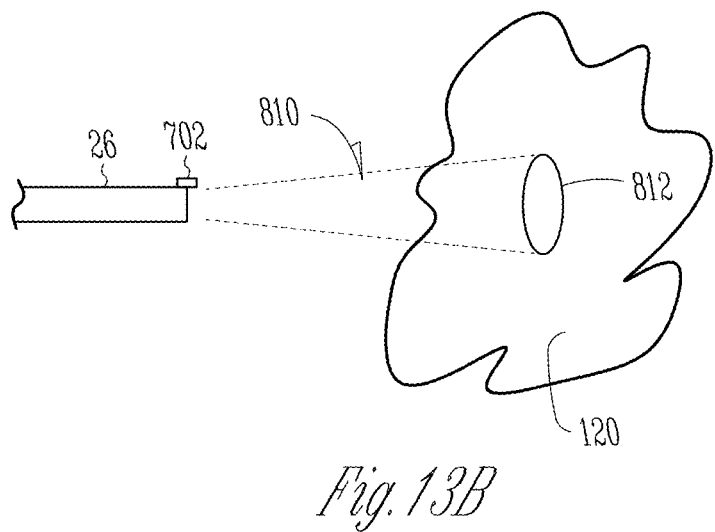
Figure 13C:
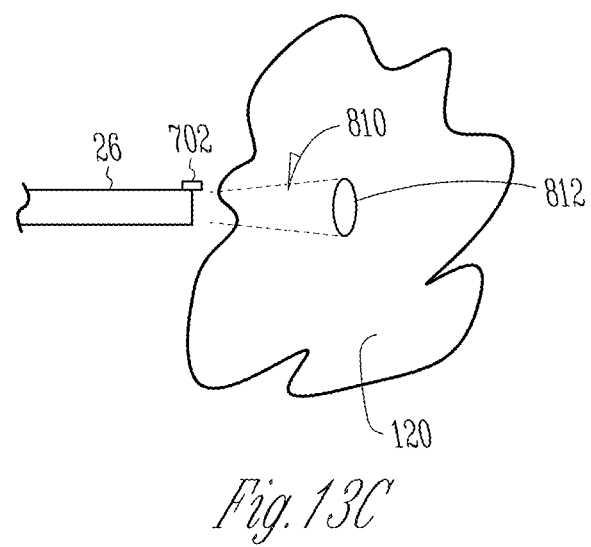

FIGS. 13A-13C are illustrative drawings to represent that a diameter size dimension of the projected circular conical light pattern 812 incident upon a tissue object 120 in the path of surgical instrument 26 provides an indication of distance between the instrument 26 and the tissue surface 120. The smaller the diameter of the circular pattern 812 incident upon the tissue 120, the closer the surgical instrument 26 is to the tissue surface. The circular conical light pattern 810 is projected in front of the surgical instrument 26 in a direction of movement of the instrument. In some embodiments, the surgical instrument 26 has a center longitudinal axis 611, and tool movement between locations involves movement of the tool 26 generally parallel to its longitudinal axis. The optical fiber 702 that acts as a source of the circular conical light pattern 810 is mounted to the surgical instrument 26 to project the projected light pattern parallel to the longitudinal axis of the first tool. Based upon where the projected light pattern falls and surgical requirements, a surgical team member may choose to continue movement of the surgical instrument 26 on its current path or change its path to avoid tissue contact or to change the tissue location where tissue contact will occur, for example.

Figure 14A:
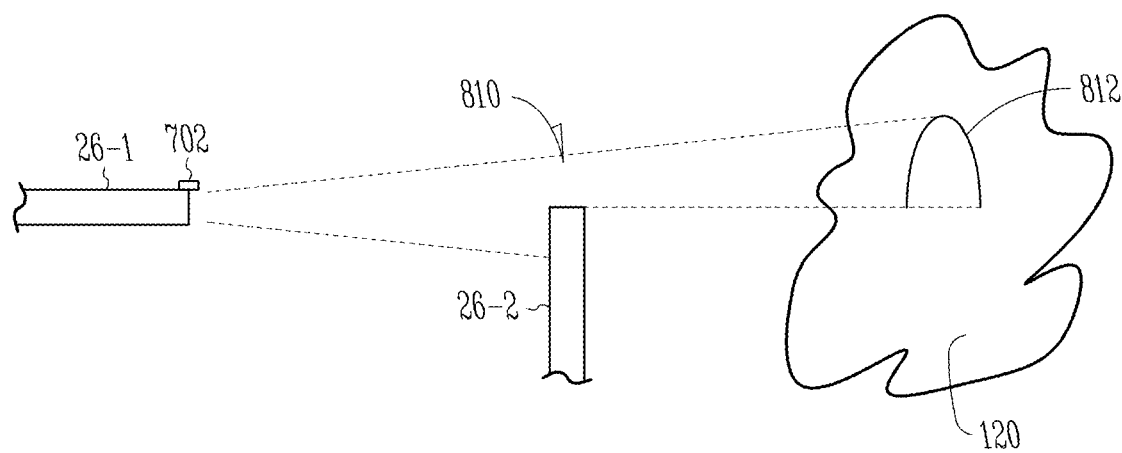
FIGS. 14A-14B are illustrative drawings to represent use of a light pattern to determine whether a first instrument is on a collision course with a second instrument.
Figure 14B:
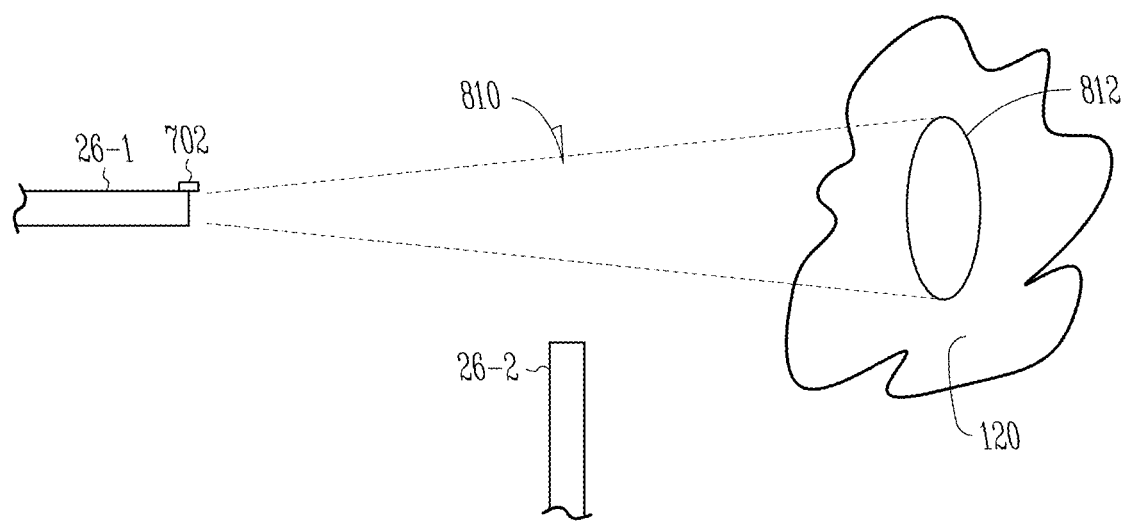

FIGS. 14A-14B are illustrative drawings to represent use of a light pattern 812 to determine whether a first instrument 26-1 is on a collision course with a second instrument 26-2. FIG. 14A shows the second instrument 26-2 in a path of the first instrument 26-1 such that a portion of the circular conical light pattern 810 emanating from an optical fiber 702 on the first instrument 26-1 is incident upon the second instrument 26-2 and therefore, does not reach the tissue surface 120. This is evident since only a portion of the circular pattern 812 is shown incident upon the tissue surface 120. The remaining portion of the pattern 812 is blocked by the second instrument 26-2 in its path. FIG. 14B shows the second instrument 26-2 moved out of the path of the first instrument 26-1 with the result that the entire circular pattern 812 is incident upon the tissue surface. It will be appreciated that a member of a surgical team may use the completeness of a circular pattern upon the tissue surface 120 as an indication of whether the path to the first surgical instrument 26-1 is blocked by the second circular instrument 26-2. Based upon this information the team member may alter the course of the first instrument 26-1 or change the position of the second instrument 26-2 to move it out of the path of the first instrument 26-1. Note that tool 26-2 may not be in the field of view of the endoscopic camera, this approach is in fact most beneficial when 26-2 is outside the camera field of view, illustration in FIG. 14B shows the global view, the endoscope may be positioned to only see tissue surface 120.

In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. A teleoperated surgical system comprising:
a support arm;
a surgical instrument, moveably mounted to the support arm, including an elongated housing having a proximal end and a distal end and having an end effector at the distal end thereof;
an actuator to impart movement to the surgical instrument;
an optical fiber, including a proximal end and a distal end, mounted to the surgical instrument to emit first light from its distal end at the distal end of the surgical instrument; and
a first light source disposed to impart the first light to the proximal end of the optical fiber at a first angle within an acceptance angle of the optical fiber;
wherein the optical fiber is disposed to emit the first light in a first conical pattern in a distal direction at the distal end of the surgical instrument.

2. The system of claim 1,
wherein the housing includes a center axis; and
wherein the optical fiber includes a center axis aligned with the center axis of the housing.

3. The system of claim 1,
wherein the first light source is disposed to inject the first light to the proximal end of the optical fiber at the proximal end of the surgical instrument.

4. The system of claim 1,
wherein the first light source includes a light emitting diode.

5. The system of claim 1,
wherein the first light source includes a laser.

6. The system of claim 1 further including:
a stereographic endoscope configured to view the surgical instrument and the first light incident upon a tissue surface within a surgical scene.

7. The system of claim 1 further including:
a stereographic endoscope configured to view the surgical instrument and the first light incident upon a tissue surface within a surgical scene; and
a user input to control the actuator imparting movement to the surgical instrument.

8. The system of claim 1,
wherein the first light source includes a pulsating light source.

9. A teleoperated surgical system comprising:
a support arm;
a surgical instrument, moveably mounted to the support arm, including an elongated housing having a proximal end and a distal end and having an end effector at the distal end thereof;
an actuator to impart movement to the surgical instrument;

an optical fiber, including a proximal end and a distal end, mounted to the surgical instrument to emit first light from its distal end at the distal end of the surgical instrument; and a first light source disposed to impart the first light to the proximal end of the optical fiber at a first angle within an acceptance angle of the optical fiber;

wherein the optical fiber is disposed to emit the first light in a first circular conical pattern in a distal direction at the distal end of the surgical instrument;

wherein the optical fiber is mounted to emit second light from its distal end at the distal end of the surgical instrument; and a second light source disposed to impart the second light to the proximal end of the optical fiber at a second angle within an acceptance angle of the optical fiber;

wherein the optical fiber is disposed to emit the second light in a second circular conical pattern in a distal direction at the distal end of the surgical instrument; and wherein the first and second circular conical patterns are concentric.

10. A method to control movement of a surgical instrument in a teleoperated surgical system comprising:

imparting light to a proximal end of an optical fiber, mounted to the surgical instrument, at a first angle within an acceptance angle of the optical fiber;

transmitting the light within the optical fiber from the proximal end of the optical fiber to a distal end of the optical fiber;

emitting the transmitted light at the distal end of the optical fiber, in a circular conical pattern to produce the circular conical pattern incident upon an object;

providing a stereographic view of the object having the circular conical pattern incident thereon;

receiving user input to adjust a position of the surgical instrument and the optical fiber mounted thereon, to thereby adjust a size of the circular conical pattern incident upon the object.

11. The method of claim 10, wherein imparting the light includes imparting light from a light emitting diode.

12. The method of claim 10, wherein imparting the light includes imparting light from a laser.

13. The method of claim 10, wherein imparting the light includes imparting pulsating light.

14. A method to control movement of a surgical instrument in a teleoperated surgical system, comprising:

producing a tissue surface depth map of a tissue surface within a field of view of a stereoscopic viewing system;

moving a surgical instrument within the field of view to change its position in relation to the tissue surface;

projecting a circular conical pattern of light, from an optical fiber mounted on the surgical instrument, onto the tissue surface at at least two positions;

determining a distance between the instrument and the tissue surface at the at least two positions by matching pixels in left and right sensors of the stereoscopic viewing system illuminated by light reflected from the circular conical pattern of light with locations within the tissue surface depth map and determining a size dimension of the projected circular conical pattern of light incident upon the tissue surface at the at least two positions.

15. The method of claim 14, wherein projecting the circular conical pattern of light from the surgical instrument onto the tissue surface includes projecting a pulsating circular conical pattern of light.

16. The method of claim 14, wherein projecting the pattern of light includes projecting light from a light emitting diode.

17. The method of claim 14, wherein projecting the pattern of light includes projecting light from a laser.

18. The method of claim 14, wherein projecting the pattern of light includes projecting pulsating light.

* * * * *